United States Patent [19]

Chu

[11] Patent Number: 4,720,602

[45] Date of Patent: Jan. 19, 1988

[54] PROCESS FOR CONVERTING $C_2$ TO $C_{12}$ ALIPHATICS TO AROMATICS OVER A ZINC-ACTIVATED ZEOLITE

[75] Inventor: Cynthia T. W. Chu, Pennington, N.J.

[73] Assignee: Mobil Oil Corporation, New York, N.Y.

[21] Appl. No.: 905,104

[22] Filed: Sep. 8, 1986

[51] Int. Cl.$^4$ .......................................... C07C 15/393
[52] U.S. Cl. .................................. 585/407; 585/415; 585/417; 585/418
[58] Field of Search ................ 585/407, 415, 417, 418

[56] References Cited

U.S. PATENT DOCUMENTS

| | | |
|---|---|---|
| 4,097,367 | 6/1983 | Haag et al. |
| 4,120,910 | 10/1978 | Chu . |
| 4,350,835 | 9/1982 | Chester et al. |
| 4,392,989 | 7/1983 | Chu et al. |
| 4,465,884 | 8/1984 | Deqnan et al. ...................... 585/407 |

FOREIGN PATENT DOCUMENTS

| | | |
|---|---|---|
| 0036683 | 1/1981 | European Pat. Off. . |
| 0021473 | 9/1981 | European Pat. Off. . |
| 0040444 | 11/1981 | European Pat. Off. . |

*Primary Examiner*—Curtis R. Davis
*Attorney, Agent, or Firm*—Alexander J. McKillop; Michael G. Gilman; Marina V. Schneller

[57] ABSTRACT

A catalytic process is provided for converting feedstocks containing $C_2$ to $C_{12}$ aliphatic hydrocarbons to aromatics by contacting said feedstocks, under conversion conditions, with a crystalline zeolite catalyst having a constraint index of about 1 to 12 and an alpha value of no higher than about 45, and a minor amount of an added metal consisting essentially of zinc, thereby converting the feedstock to aromatics.

18 Claims, No Drawings

PROCESS FOR CONVERTING $C_2$ TO $C_{12}$ ALIPHATICS TO AROMATICS OVER A ZINC-ACTIVATED ZEOLITE

BACKGROUND OF THE INVENTION

Field of the Invention

This invention relates to a process for the conversion of a gaseous paraffinic feed containing a major proportion of $C_2$ to $C_{12}$ aliphatic hydrocarbons to aromatics in the presence of a crystalline zeolite catalyst containing an added metal consisting essentially of zinc.

Zeolites and alumina have been used in the past in the preparation of catalysts for the production of aromatic hydrocarbons from aliphatic hydrocarbons. The aliphatic hydrocarbon is passed over the catalyst at an elevated temperature in the liquid or vapor phase. Zeolites of various types have been suggested for the preparation of such catalysts. Examples of such zeolites are mordenite and the ZSM varieties, some of which contain zinc as ions which have been impregnated on the zeolite substrate or for which the original cations have been exchanged. However, it has sometimes been considered desirable to improve the yields of aromatic hydrocarbons when using such catalysts.

U.S. Pat. No. 4,097,367 teaches the catalytic conversion of olefinic naphthas which contain diolefins over a special catalyst to yield a product stream which contains little or no non-aromatics boiling in the range of benzene, toluene and xylene. The catalyst is a combination of zinc and a metal from Groups IB and VIII of the Periodic Table with a crystalline aluminosilicate zeolite having a silica-alumina ratio greater than 12 and a Constraint Index not less than one nor greater than 12.

U.S. Pat. No. 4,120,910 discloses that aromatic compounds can be produced by contacting, in the absence of added air or oxygen under suitable conversion conditions, a gaseous, paraffinic feed stock containing a high percentage of ethane with a ZSM-5 type crystalline aluminosilicate zeolite catalyst having incorporated therein a minor amount of a metal or metal oxide from Group VIII, IIB, or IB of the Periodic Table. Especially preferred is a zinc-copper mixture.

U.S. Pat. No. 4,350,835 teaches a catalytic process for converting a feedstock comprising a high percentage of ethane to aromatics employing as a catalyst a zeolite with a silica-alumina ratio of at least 12 and having incorporated therein a minor amount of gallium. The patent also discloses, for comparison purposes a catalyst containing 1% zinc and 0.25% copper supported on a ZSM-5 zeolite having a silica to alumina ratio of 40.

U.S. Pat. No. 4,392,989 shows the aromatization of paraffin feeds containing $C_2$–$C_{12}$ hydrocarbons using a catalyst comprising a zeolite containing zinc in combination with gallium or palladium.

SUMMARY OF THE INVENTION

Briefly stated, this invention comprises a process for producing aromatic compounds including contacting under suitable conversion conditions a feed containing a major proportion of $C_2$–$C_{12}$ aliphatic hydrocarbons with a ZSM type crystalline aluminosilicate zeolite catalyst having a low acid activity indicated by an alpha value no greater than about 45, and an added metal consisting essentially of zinc, whereby a portion of the aliphatic compounds present in said feed is converted to aromatic compounds.

DESCRIPTION OF SPECIFIC EMBODIMENTS

Accordingly, the present invention is a process for producing aromatic hydrocarbons comprising bringing into contact at an elevated temperature a hydrocarbon feedstock containing a major proportion of $C_2$–$C_{12}$ aliphatic hydrocarbons with a catalyst composition comprising a zeolite having a low acid activity as indicated by an alpha value no greater than about 45, and an added metal consisting essentially of zinc deposited thereon and/or whose cations have been exchanged with ions of zinc. Preferably, the added metal consists solely of zinc.

The degree of zeolite catalyst activity for all acid catalyzed reactions can be measured and compared by means of "alpha value". The alpha value reflects the relative activity of the catalyst with respect to a standard high activity silica-alumina cracking catalyst. To determine the alpha value as such term is used herein, n-hexane conversion is determined at a suitable temperature between about 550° F. to 1000° F., preferably at 1000° F. Conversion is varied by variation in space velocity such that a conversion level of up to about 60 percent of n-hexane is obtained, which is converted to a rate constant per unit volume of zeolite, and compared with that of the standard silica-alumina catalyst normalized to a reference activity of 1000° F. Catalytic activity of the catalyst is expressed as a multiple of the silica-alumina standard. The standard silica-alumina reference catalyst contains about 10 percent $Al_2O_3$ and the reminder $SiO_2$. This method of determining alpha value, modified as described above, is more fully described in the Journal of Catalysis, Vol. VI, pp. 278–287, 1966.

The term "added metal" is intended to cover those metallic elements not present in the zeolite as synthesized but added subsequently by means of a treatment such as impregnation, or ion-exchange. Such term thus does not include those metals such as aluminum or alkali metal, e.g. sodium, present as a result of the initial synthesis of the zeolite.

The term "consisting essentially" is intended to exclude any added metal other than zinc which would have the effect of changing the basic and novel characteristics of the processes and catalysts disclosed and claimed herein, or which would change the nature and intent of such processes and catalysts.

The zinc in the catalyst composition may be present as ions if cations in the aluminosilicate support have been exchanged with zinc ions. In the case where the cations in the zeolite have been exchanged for zinc ions, the ions are suitably provided as an aqueous solution of zinc-containing metal salts such as for instance zinc sulfate, nitrate or chloride. Such catalysts may be produced by conventional ion exchange techniques and the catalysts so produced are subsequently dried. For example, an aqueous solution of a zinc compound such as a zinc nitrate may be placed in contact with the zeolite at ambient or elevated temperature, e.g. by refluxing. The exchanged zeolite is then separated by decantation followed by filtration, washed several times with deionized water and finally dried. Before addition to the aqueous solution of the zinc compound, the zeolite may be acid treated.

The process of the present invention may be carried out using catalysts in which zinc is impregnated on the surface of the zeolite or is ion-exchanged with the cations of the zeolite. Where the catalyst composition is prepared by using a compound of zinc which ionizes in aqueous solution, for example zinc nitrate, some of the zinc ions are generally exchanged with the cations in the zeolite even if the preparation was directed to impregnation of the zeolite. Whichever method of catalyst preparation is used, the amount of zinc present in the catalyst composition, (zinc plus zeolite) may vary for instance between about 0.1 and 10%, preferably between about 0.5 and 5% by weight.

Although the zeolites utilized in the process may have extremely low alumina contents, e.g. silica to alumina mole ratios exceeding about 220, they are nevertheless very active. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

The low alpha value (not greater than about 45) catalyst may be prepared as-synthesized, or by decreasing the alpha value of a high alpha value catalyst, e.g. by steaming, dealuminizing or framework exchange procedures.

The alpha value decreases with a rise in the silica/alumina ratio of the the zeolite and, in the absence of any specific treatment to reduce its acidity, the protonated or hydrogen form of the zeolite having an alpha value within the limits of this invention will generally have a silica/alumina ratio of at least 220. However, the acidity and thus the alpha value of a zeolite having a silica-alumina ratio below 220 may be reduced to the desired level by the means mentioned previously, e.g. steaming, dialuminizing or framework exchange procedures. If such means are used to reduce below 45 the alpha value of a zeolite having a silica-alumina ratio of below 220, then such zeolite is contemplated for use in this invention. It should be noted also that since some acidity of the catalyst is necessary in order to obtain sufficient conversion of the feed hydrocarbons, the alpha value of the catalyst will in most cases be at least about 0.5.

The techniques of steaming zeolites to obtain desired alpha values are known to those skilled in the art.

When the treating atmosphere is steam, temperatures may be used extending from about 500° F. to about 1800° F. depending on the steam pressure, with the use of higher pressure requiring a lower temperature. This treatment is carried on for a period of time sufficient to effect the desired reduction in alpha value. Generally, such period will be between about ½ hour and 100 hours. A steam treating atmosphere may be employed which is 100 percent steam or steam admixed with a gas which is substantially inert with respect to the zeolite. It is contemplated that the treatment will generally be effected at atmospheric pressure, but pressures ranging from sub-atmospheric pressure to several hundred atmospheres may be employed. With the use of elevated pressures, temperatures in the lower region of the above-specified range will usually be applicable in achieving the desired reduction in alpha value of the zeolite under treatment. Thus, it has been found, that at elevated steam pressure, the temperature of treatment can be reduced substantially to achieve the same degree of modification.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with silica to alumina mole ratios of at least about 220 are useful, it is preferred in some instances to use zeolites having substantially higher silica/alumina ratios, e.g. 880 and above. Such "high-silica" or "highly siliceous" zeolites are intended to be included within this description.

The members of the class of zeolites useful herein have an effective pore size of generally from about 5 to about 8 angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolites is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g. less than 5 angstroms. On the other hand, zeolites which provide relatively free access to the internal zeolite structure have a low value for the Constraint Index, and usually pores of large size, e.g. greater than 8 angstroms. The method by which Constraint Index is determined is described fully in U.S. Pat. No. 4,016,218, incorporated herein by reference for details of the method.

Constraint Index (CI) values for some typical materials are:

|  | CI (at test temperatures) | |
| --- | --- | --- |
| ZSM-4 | 0.5 | (316° C.) |
| ZSM-5 | 6–8.3 | (371° C.–316° C.) |
| ZSM-11 | 5–8.7 | (371° C.–316° C.) |
| ZSM-12 | 2.3 | (316° C.) |
| ZSM-20 | 0.5 | (371° C.) |
| ZSM-22 | 7.3 | (427° C.) |
| ZSM-23 | 9.1 | (427° C.) |
| ZSM-34 | 50 | (371° C.) |
| ZSM-35 | 4.5 | (454° C.) |
| ZSM-38 | 2 | (510° C.) |
| ZSM-48 | 3.5 | (538° C.) |
| ZSM-50 | 2.1 | (427° C.) |
| TMA Offretite | 3.7 | (316° C.) |
| TEA Mordenite | 0.4 | (316° C.) |

-continued

| | CI | (at test temperatures) |
|---|---|---|
| Clinoptilolite | 3.4 | (510° C.) |
| Mordenite | 0.5 | (316° C.) |
| REY | 0.4 | (316° C.) |
| Amorphous Silica-alumina | 0.6 | (538° C.) |
| Dealuminized Y | 0.5 | (510° C.) |
| Erionite | 38 | (316° C.) |
| Zeolite Beta | 0.6–2.0 | (316° C.–399° C.) |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood to those skilled in the art that the CI, as utilized herein, while affording a highly useful means for characterizing the zeolites of interest is approximate, taking into consideration the manner of its determination, with the possibility, in some instances, of compounding variable extremes. However, in all instances, at a temperature within the above-specified range of 290° C. to about 538° C., the CI will have a value for any given zeolite of interest herein within the approximate range of 1 to 12.

The class of zeolites defined herein is exemplified by ZSM-5, ZSM-11, ZSM-12, ZSM-23, ZSM-35, ZSM-38, ZSM-48, and other similar materials. The compositions, methods of preparation, and X-ray diffraction patterns of these zeolites are typified in the following patents: ZSM-5 in U.S. Pat. No. 3,702,886 and Re. No. 29,948; ZSM-11 in U.S. Pat. No. 3,709,979; ZSM-12 in U.S. Pat. No. 3,832,449; ZSM-23 in U.S. Pat. No. 4,076,842; ZSM-35 in U.S. Pat. No. 4,016,245; ZSM-38 in U.S. Pat. No. 4,046,859 and ZSM-48 in U.S. Pat. No. 4,350,835. The entire disclosures of these patents are incorporated by reference insofar as their disclosures are necessary to identify the respective zeolites.

It is to be understood that by incorporating by reference the foregoing patents to describe examples of specific members of the class with greater particularity, it is intended that identification of the therein disclosed crystalline zeolites be resolved on the basis of their respective X-ray diffraction patterns. As discussed above, the present invention contemplates utilization of such catalysts having an alpha value no higher than about 45 and as low as 0.5, and wherein the mole ratio of silica to alumina of the as synthesized catalyst in the absence of treatment to reduce its alpha value is at least about 220 and may be as high as about 26,000, preferably as high as about 5000. The incorporation of the identified patents should therefore not be construed as limiting the disclosed crystalline zeolites to those having the specific alpha values and silica-alumina mole ratios discussed therein, it now being known that such zeolites may have much lower alpha values and higher silica-alumina ratios and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at about 540° C. for one hour, for example, followed by base exchange with ammonium salts followed by calcination at about 540° C. in air. The presence of organic cations in the forming solution may not be absolutely essential to the formation of this type zeolite; however, the presence of these cations does appear to favor the formation of this special class of zeolite. In many cases, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, an alpha value no greater than 45 and as low as 0.5, a silica to alumina mole ratio in the absence of treatment to reduce its alpha value of at least about 220 and up to about 26,000, and a dried crystal density of not less than about 1.6 grams per cubic centimeter. The dry density for known structures may be calculated from the number of silicon plus aluminum atoms per 1000 cubic angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, Apr. 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with zinc as mentioned previously.

In practicing a particularly desired chemical conversion process, it may be useful to composite the above-described crystalline zeolite with a matrix comprising another material resistant to the temperature and other conditions employed in the process. Such matrix material is useful as a binder and imparts greated resistance to the catalyst for the severe temperature, pressure and reactant feed stream velocity conditions encountered in many conversion processes.

Useful matrix materials include both synthetic and naturally occurring substances, as well as inorganic materials such as clays, and inorganic oxides such as silica and/or metal oxides and mixtures thereof. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, kickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica, silica-alimina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The feed stream to the process of this invention contains at least 50% by weight of at least one aliphatic hydrocarbon containing 2 to 12 carbon atoms. The hydrocarbon may be straight chain, open chain or cyclic and may be saturated or unsaturated. Some contemplated hydrocarbons are ethane, propane, propylene, n-butane, n-butenes, isobutane, isobutene, straight-and branch chain hexanes, hexenes, octanes, octenes, decanes and decenes, cyclohexane and cyclohexene.

The process of this invention is conducted so that a feed containing a high percentage, i.e. at least 50 wt. % of $C_2$-$C_{12}$ aliphatic hydrocarbons is contacted with a suitable zeolite catalyst in a reaction zone, such as, for example, a fixed bed of catalyst composition under effective conversion conditions. In a typical embodiment of the process of this invention, the feed stream is introduced into the reaction zone at a temperature within the range of 482° C. (900° F.) and about 760° C. (1400° F.), a pressure within the range of $1 \times 10^5$ pascal (atmospheric pressure) to $26.6 \times 10^5$ pascal (400 psig) and a LHSV of 0.1 to 5.

Preferred temperatures for the process of this invention fall within the range of about 482° C. (900° F.) to about 676.7° C. (1250° F.) and preferred pressures fall within the range of $1 \times 10^5$ pascal (one atmosphere) to $7.9 \times 10^5$ pascal (100 psig). A preferred LHSV is between 0.3 and 3.

The effluent from the reaction zone is separated and distilled to remove the desired aromatic product and the remainder is recycled for further reaction.

The following examples further illustrate the invention. Example 1 is an embodiment of processes carried out within the invention, while Example 2 (Comparative) is a similar embodiment which shows the results obtained when a high acid activity catalyst (alpha value =150) is used which is outside the scope of the invention.

EXAMPLE 1

This example illustrates the preparation and use of a zinc-containing zeolite catalyst under the invention wherein the zinc is deposited on the zeolite by impregnation.

Five grams of a hydrogen or acid-base ZSM-5 zeolite having an alpha value of about 5 and a silica-alumina ratio of about 1000, and 0.23 grams of $Zn(NO_3)_2 \cdot 6H_2O$, were mixed with 10 cc of water. The mixture was then dried and calcined at 538° C. (in air) for 6 hours. The final catalyst contained about 1.0 wt% of added zinc.

This catalyst was tested for aromatization activity by loading it into a reactor and introducing n-hexane at a temperature of 538° C. (1000° F.), atmospheric pressure, and an LHSV of 0.59. After various times on stream, the product was analyzed. Hydrogen and light gases ($C_1$-$C_3$) were analyzed by a refinery gas analysis GC, $C_3$+gases were analyzed on a n-octane-porasil C column, and liquid products were analyzed on a DB-1 Durabond capillary column. The results are shown in the table where the numbers all signify weight percent of product except as indicated, "$C_1+C_2$" is the total of methane and ethane, "$C_2=+$" is the total of ethylene and higher aliphatics and "Aromatics Selectivity" is defined as follows.

$$\frac{\text{Aromatics yield (wt. \%)}}{C_1 + C_2 \text{ (wt. \%)} + \text{aromatics yield (wt. \%)}}$$

EXAMPLE 2

(Comparative)

The procedure of Example 1 was followed except that the ZSM-5 zeolite had an alpha value of about 150 and a silica/alumina ratio of 70. The results are shown in the table.

TABLE

| Example | 1 | 2 (Comparative) |
|---|---|---|
| $H_2$ | 2.27 | 4.12 |
| Methane | 4.54 | 14.91 |
| Ethane | 5.86 | 26.93 |
| Propane | 6.05 | 1.20 |
| n-Butane | 1.68 | 0.00 |
| i-Butane | 1.18 | 0.00 |
| n-Pentane | 0.14 | 0.00 |
| i-Pentane | 0.18 | 0.00 |
| n-Hexane | 30.51 | 3.28 |
| $C_6$ Aliphatics + P + O | 0.62 | 0.00 |
| Ethylene | 6.41 | 0.39 |
| Propylene | 9.16 | 0.15 |
| $C_4$ Olefins | 4.24 | 0.00 |
| $C_5$ Olefins | 0.39 | 0.00 |
| Benzene | 4.80 | 20.83 |
| Toluene | 9.67 | 16.74 |
| $C_8$ Aromatics | 8.01 | 7.37 |
| $C_9$ Aromatics | 2.07 | 1.25 |
| $C_{10}$ Aromatics | 1.35 | 1.64 |
| $C_{11}$ Aromatics | 0.88 | 1.18 |
| $C_1 + C_2$ | 10.64 | 43.64 |
| Aromatics | 27.40 | 51.12 |
| $C_2=+$ | 61.96 | 5.25 |
| Aromatics Selectivity | 72.03 | 53.95 |

As shown in the table, the catalyst and process of this invention utilizing a zeolite with a relatively low alpha value and high silica/alumina ratio resulted in higher aromatics selectivity and less undesirable by-products such as methane and ethane than when a more conventional zeolite having a higher alpha value and lower silica/alumina ratio outside the scope of the invention was employed.

I claim:

1. A process for producing aromatic compounds which comprises contacting under conversion conditions, a feed containing at least 50 weight percent of $C_2$ to $C_{12}$ aliphatic hydrocarbons with a low acid activity catalyst comprising a crystalline zeolite characterized by a Constraint Index within the approximate range of 1 to 12 and an alpha value no higher than about 45, and an added metal consisting essentially of between from about 0.1 to about 10 percent of zinc based on the total weight of catalyst, whereby aliphatic hydrocarbons present in said feed are converted to aromatic compounds, and recovering said aromatic compounds.

2. The process of claim 1 wherein said zeolite has a silica/alumina ratio of at least about 220.

3. The process of claim 1 wherein said alpha value of said catalyst is in the range of about 0.5 to 45.

4. The process of claim 2 wherein said silica/alumina ratio is in the range of about 220 to 5000.

5. The process of claim 1 wherein the conversion conditions include a temperature of from about 482° C. to about 760° C., a pressure of from about $1 \times 10^5$ to about $28.6 \times 10^5$ pascal and an LHSV of from about 0.1 to about 5.

6. The process of claim 1 wherein said crystalline zeolite is selected from the group consisting of ZSM-5, ZSM-11, ZSM-12, ZSM-35, ZSM-38 and ZSM-48.

7. The process of claim 1 wherein the concentration of zinc in said catalyst is between about 0.5 and about 5 percent by weight.

8. The process of claim 4 wherein said zeolite is ZSM-5, said catalyst is composited with a porous matrix material in a proportion of between about 5 and about 80 percent by weight of catalyst composition in the dry composite, and conversion conditions include a temperature of from about 482° C. to about 676.7° C., a pressure of from about $1 \times 10^5$ to about $7.9 \times 10^5$ pascal and an LHSV of about 0.3 to about 3.

9. The process of claim 8 wherein said zeolite as synthesized has an alpha value of over 45 which is reduced to below 45 by an after-treatment.

10. The process of claim 9 wherein said after-treatment is steaming.

11. The process of claim 1 wherein said zeolite is composited with a matrix material comprising at least one clay or inorganic oxide.

12. A process for producing aromatic compounds which comprises contacting under conversion conditions, a feeding containing at least 50 wt % of $C_2$ to $C_{12}$ aliphatic hydrocarbons with a low acid activity catalyst comprising ZSM-5 having an alpha value no higher than about 45, in combination with an added metal consisting essentially of between from about 0.1 to about 10 percent of zinc based on the total weight of catalyst, whereby aliphatic hydrocarbon present in said feed are converted to aromatic compounds, and recovering said aromatic compounds.

13. The process of claim 12, wherein said zeolite has a silica/alumina ratio of at least about 220.

14. The process of claim 12, wherein said alpha value of said catalyst is in the range of about 0.5 to 45.

15. The process of claim 13, wherein said silica/alumina ratio is in the range of about 220 to 5000.

16. The process of claim 12, wherein the conversion conditions include a temperature of from about 482° C. to about 760° C., a pressure from about $1 \times 10^5$ to about $28.6 \times 10^5$ pascal and an LHSV from about 0.1 to about 5.

17. The process of claim 12, wherein the concentration of zinc and said catalyst is between about 0.5 and 5 percent by weight.

18. The process of claim 15, wherein the zeolite is composited with a porous matrix material in a proportion of between about 5 and about 80 percent by weight of the catalyst composition in the dry composite and wherein conversion conditions include a temperature of from about 482° C. to about 676.7° C., a pressure of from about $1 \times 10^5$ to about $7.9 \times 10^5$ pascal and an LHSV of about 0.3 to about 3.

* * * * *